US010206661B2

(12) United States Patent
Mammone

(10) Patent No.: US 10,206,661 B2
(45) Date of Patent: Feb. 19, 2019

(54) ULTRASOUND WITH AUGMENTED VISUALIZATION

(75) Inventor: Richard J. Mammone, Warren, NJ (US)

(73) Assignee: Empire Technology Development LLC, Wilmington, DE (US)

(*) Notice: Subject to any disclaimer, the term of this patent is extended or adjusted under 35 U.S.C. 154(b) by 1507 days.

(21) Appl. No.: 13/884,256

(22) PCT Filed: Sep. 7, 2012

(86) PCT No.: PCT/US2012/054239
§ 371 (c)(1),
(2), (4) Date: May 8, 2013

(87) PCT Pub. No.: WO2014/039051
PCT Pub. Date: Mar. 13, 2014

(65) Prior Publication Data
US 2014/0073922 A1   Mar. 13, 2014

(51) Int. Cl.
A61B 8/08 (2006.01)
A61B 8/00 (2006.01)
A61B 8/13 (2006.01)

(52) U.S. Cl.
CPC .............. *A61B 8/5223* (2013.01); *A61B 8/13* (2013.01); *A61B 8/463* (2013.01); *A61B 8/565* (2013.01); *A61B 8/085* (2013.01)

(58) Field of Classification Search
None
See application file for complete search history.

(56) References Cited

U.S. PATENT DOCUMENTS

| 4,830,015 | A | | 5/1989 | Okazaki |
| 5,361,767 | A | * | 11/1994 | Yukov ............... A61B 8/0858 600/442 |
| 6,238,342 | B1 | | 5/2001 | Feleppa et al. |
| 2004/0220465 | A1 | | 11/2004 | Cafarella |
| 2005/0220265 | A1 | | 10/2005 | Besson |
| 2009/0087045 | A1 | | 4/2009 | Partain et al. |
| 2009/0318804 | A1 | | 12/2009 | Avital et al. |
| 2011/0020858 | A1 | * | 1/2011 | Shin .................... C12N 13/00 435/29 |
| 2011/0060222 | A1 | | 3/2011 | Thittai et al. |
| 2016/0022235 | A1 | * | 1/2016 | Ning ................... A61B 6/032 378/4 |

FOREIGN PATENT DOCUMENTS

WO   WO 2007/085073   8/2007

OTHER PUBLICATIONS

Baldeweck et al., "Application of Autoregressive Spectral Analysis for Ultrasound Attenuation Estimation: Interest in Highly Attenuating Medium," IEEE Trans. Ultrason., Ferroelect., Freq. Contro., 1995, pp. 99-110, vol. 42 (1).

(Continued)

*Primary Examiner* — Michael Carey
*Assistant Examiner* — Shahdeep Mohammed

(57) ABSTRACT

Embodiments provided herein generally relate to improved ultrasound visualization. In some embodiments, interoperative ultrasound displays may be enhanced for more accurate identification of cancerous and non-cancerous tissues.

22 Claims, 7 Drawing Sheets

(56) References Cited

OTHER PUBLICATIONS

Dong et al., "In Vivo Measurements of Frequency-Dependent Attenuation in Tumors of the Liver," Journal of Clinical Ultrasound, Mar./Apr. 1994, pp. 167-174, vol. 22 (3).
Doyle et al., "High-Frequency Ultrasound for Intraoperative Margin Assessments in Breast Conservation Surgery: A Feasibility Study," BMC Cancer, 2011, 51 pages, vol. 11.
Giralt et al., "Time-Varying Autoregressive Spectral Estimation for Ultrasound Attenuation in Tissue Characterization," IEEE Trans. Ultrason., Ferroelect., Freq. Contr., 1998, pp. 650-659, vol. 45 (3).
He,"Accoustic Attenuation Estimation for Soft Tissue Ultrasound Echo Envelop Peaks," IEEE Trans., Ultra. Ferroelec. Freq. Contr., 1989, pp. 197-203, vol. 36 (2).
He et al., "Application of Stochastic Analysis to Ultrasonic Echoes-Estimation of Attenuation and Tissue Heterogeneity from Peaks of Echo Envelop," Am., 1986, pp. 526-534, vol. 79 (2).
He, "On The Estimation of Acoustic Attenuation Coefficient from Peaks of Echo Envelope," Acous. Soc. Aw., May 1988, pp. 1919-1926, vol. 83 (5).
He, "Statistical Relationship Between Ultrasound Echo Envelop and Envelop Peak," Ultrason., Imag., 1988, pp. 265-274, vol. 10.
International Search Report and Written Opinion received in International Application No. PCT/US2012/054239, dated Nov. 16, 2012, filed on Sep. 7, 2012.
Jirik et al., "Ultrasound Attenuation Imaging," Journal of Electrical Engineering, 2004, pp. 180-187, vol. 55 (7-8).
Kim et al., "Estimation of Ultrasound Attenuation from Broadband Echo-Signals Using Bandpass Filtering," IEEE Trans. Ultrason., Ferroelect., Freq. Contr., 2008, pp. 1153-1159, vol. 55 (5).
Li et al., "Estimation of Local Attenuation and Its Application to Rationalized Gain Control," IEEE iCBBE, 2007, pp. 1267-1270, vol. 2.
Martinsson et al, "Model-Based Phase Velocity and Attenuation Estimation in Wideband Ultrasonic Measurement Systems," Ultrasonic, Ferroelectrics and Frequency Control, IEEE Transactions, Jan. 2007, pp. 138-146, vol. 54 (1).
Parker et al., "Measurement of Ultrasonic Attenuation within Regions Selected from B-Scan Images," IEEE Trans. Biomedical Engineering, 1983, pp. 431-437, vol. 8.
Peters et al., "Estimation of Local Attenuation from Multiple View Using Compensated Video Signals," Acustica, 1993, pp. 251-258, vol. 79.
Salim et al., "Measurement of Ultrasound Attenuation for Normal and Pathological Mice Breast Tissue Using 10MHz Ultrasound Wave," Advances in Visualization, Imaging, and Simulation, $3^{RD}$ WSEAS International Conference on Visualization, Imaging and Simulation (VIS '10) Faro, Portugal, Nov. 3-5, 2010.
Vicas C, Nedevschi S, Lupsor M, Badea R, Grigorescu, M. Steatohepatitis detection from ultrasound images usingattenuation and backscattering coefficients. J Automation,Computers, Applied Mathematics 2007;16:20-26.
Wagnetz et al., "Intraoperative Ultrasound of the Liver in Primary and Secondary Hepatic Malignancies: Comparison with Preoperative 1.5-T MRI and 64-MDCT," AJR AM J. Roentgenol, Mar. 2011, pp. 562-568, vol. 196 (3).
Wear, "A Gaussian Framework for Modeling Effects of Frequency-Dependent Attenuation, Frequency-Dependent Scattering, and Gating," IEEE Trans. Ultrason., Ferroelect., Freq. Contr., 2002, pp. 1572-1582, vol. 49 (11).
Wendler et al., "Real-Time Fusion of Ultrasound and Gamma Probe for Navigated Localization of Liver Metastases," Med Imag. Comput. Comput. Assist. Inter., 2007, pp. 252-60, vol. 10 (Pt 2).

* cited by examiner

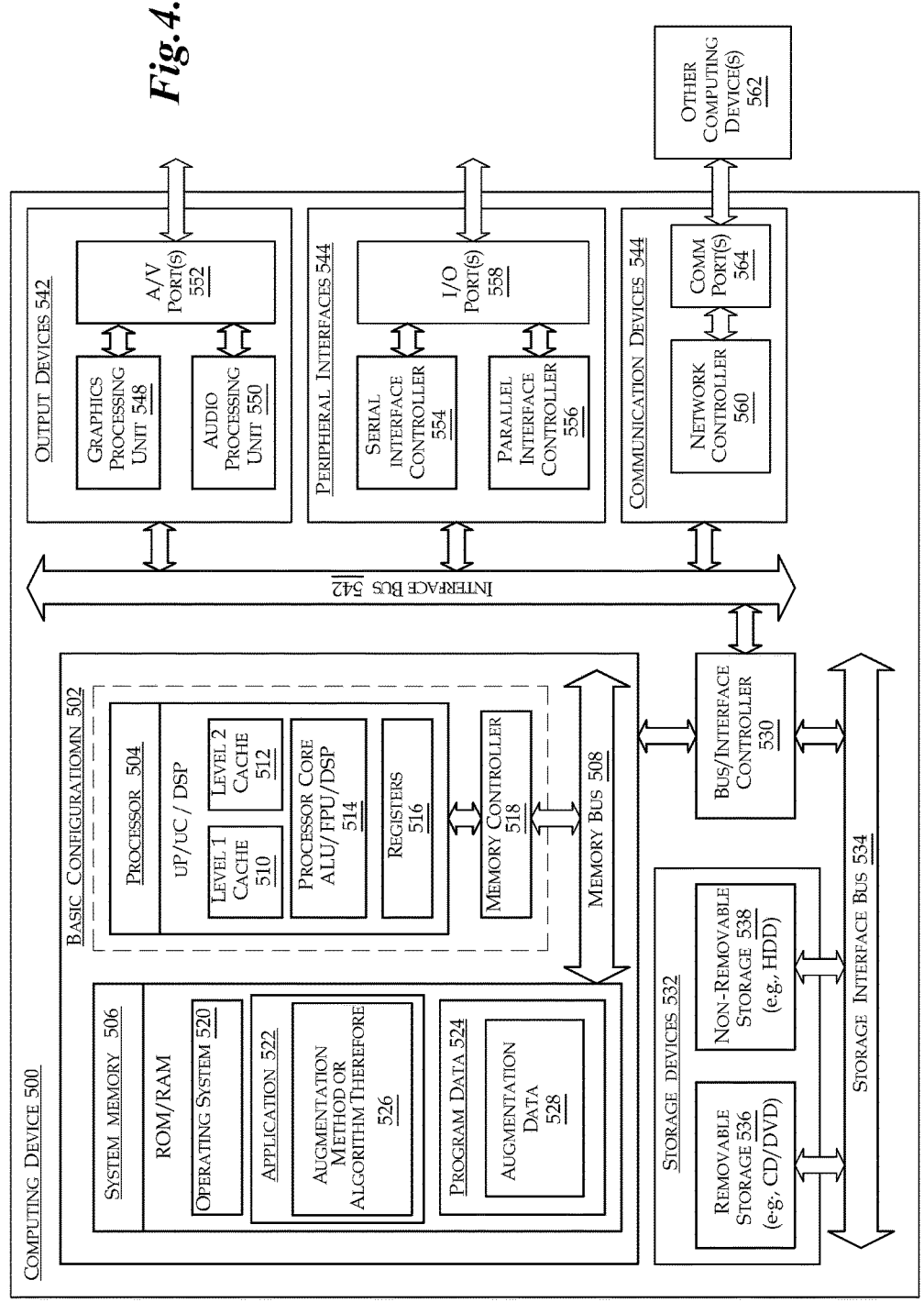

600 A computer program product.

602 A signal bearing medium.

604 at least one of one or more instructions for obtaining a mean attenuation coefficient representing attenuation of an ultrasound signal incident upon a region of interest of a tissue;

one or more instructions for determining a first probability, wherein the first probability describes a probability that the tissue is cancerous, and wherein the first probability is determined based at least upon the obtained mean attenuation coefficient;

one or more instructions for determining a second probability, wherein the second probability describes a probability that the tissue is non-cancerous, and wherein the second probability is determined at least based upon the obtained mean attenuation coefficient; or one or more instructions for generating a likelihood value (Lv) that the tissue is cancerous based upon the first and second probabilities.

606 a computer-readable medium.

608 a recordable medium.

610 a communications medium.

*Fig.5.*

ULTRASOUND WITH AUGMENTED VISUALIZATION

CLAIM FOR PRIORITY

This application is the U.S. national phase entry under 35 U.S.C. § 371 of PCT/US2012/054239, filed Sep. 7, 2012, the entire disclosure of which is hereby incorporated by reference herein.

TECHNICAL FIELD

Embodiments presented herein generally relate to the detection of cancerous cells and/or various tissues.

BACKGROUND

Cancer generally refers to the group of diseases that are characterized by uncontrolled growth and spread of abnormally functioning cells in the tissue of an organism. For the year 2012, American Cancer Society estimates that approximately 1,638,910 new cases of cancer will be diagnosed in the United States and approximately 577,190 Americans will die due to cancer. This mortality estimate places cancer as the second-most common cause of death in the United States, exceeded only by heart disease.

Cancer survival rates have risen with the advancement of various diagnostic techniques that are capable of detecting cancers at earlier stages. For example, the 5-year survival rate for all cancers detected between 1975-1977 in the United States was approximately 49% while, more than 25 years later, the 5-year survival rates for all cancers diagnosed between 2001-2007 rose to approximately 67%.

SUMMARY

In some embodiments, a system for identifying cancerous tissue is provided. The system can include a data store that maintains statistical information regarding the distribution of mean attenuation coefficients of ultrasound signals for a plurality of tissues in cancerous and non-cancerous states. The system can further include a computing device in communication with the data store. The computing device can be operative to obtain a mean attenuation coefficient representing attenuation of an ultrasound signal incident upon a region of interest of a tissue. The computing device can be further operative to determine a first probability that the tissue is cancerous, where the first probability is determined based at least upon the obtained mean attenuation coefficient and the statistical mean attenuation coefficient information for the tissue in the cancerous state maintained in the data store. The computing device can be further operative to determine a second probability that the tissue is non-cancerous, where the second probability is determined at least based upon the obtained mean attenuation coefficient and the statistical mean attenuation coefficient information for the tissue in the non-cancerous state maintained in the data store. The computing device can be additionally operative to generate a likelihood value ($L_v$) that the tissue is cancerous based upon the first and second probabilities.

In some embodiments, a computer-implemented method for identifying cancerous tissue is provided. The computer-implemented method can include electronically obtaining, at a computing device, a mean attenuation coefficient representing attenuation of an ultrasound signal incident upon a region of interest of a tissue. The computer-implemented method can further include calculating, by the computing device, a first probability, where the first probability describes a probability that the tissue is cancerous. The computer-implemented method can further include calculating, by the computing device, a second probability, where the second probability describes a probability that the tissue is non-cancerous. The computer-implemented method can further include determining, by the computing device, a likelihood that the tissue is cancerous based upon a ratio of the first and second probabilities.

In some embodiments, a computer-readable medium can be provided. The computer readable medium can store software instructions that are readable by a computing system. The software instructions can be executable on the computing system in order to cause the computing system to perform operations. The computing system can further perform an operation of obtaining a mean attenuation coefficient representing attenuation of an ultrasound signal incident upon a region of interest of a tissue. The computing system can further perform an operation of determining a first probability, where the first probability describes a probability that the tissue is cancerous, and where the first probability is determined based at least upon the obtained mean attenuation coefficient. The computing system can additionally perform an operation of determining a second probability, where the second probability describes a probability that the tissue is non-cancerous, and where the second probability is determined at least based upon the obtained mean attenuation coefficient. The computing system can further perform an operation of generating a likelihood value ($L_v$) that the tissue is cancerous based upon the first and second probabilities.

BRIEF DESCRIPTION OF THE DRAWINGS

FIG. 4 is a block diagram illustrating an example computing device.

FIG. 5 is a schematic illustrating an example computer program product.

DETAILED DESCRIPTION

Figure 1A:
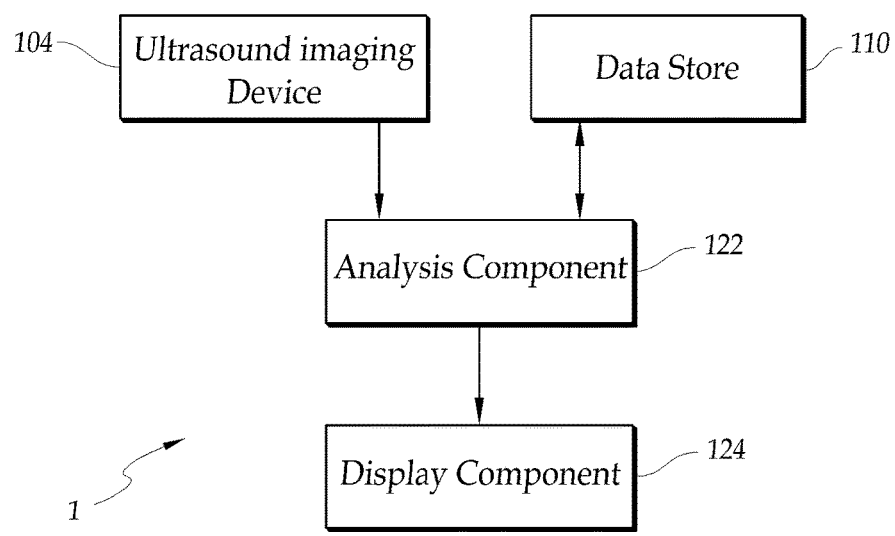
FIG. 1A is a schematic illustration of a purpose built device of some embodiments of a cancer detection system.

In the following detailed description, reference is made to the accompanying drawings, which form a part hereof. In the drawings, similar symbols may identify similar components, unless context dictates otherwise. The embodiments described in the detailed description, drawings, and claims are not meant to be limiting. Other embodiments can be utilized, and other changes can be made, without departing from the spirit or scope of the subject matter presented herein. It may be readily understood that the aspects of the present disclosure, as generally described herein, and illustrated in the Figures, can be arranged, substituted, combined, separated, and designed in a wide variety of different configurations, all of which are explicitly contemplated herein.

Ultrasound is a non-invasive imaging technique that employs cyclic pressure waves having a frequency greater than or equal to about 20 kHz for visualization of internal structures of objects. For example, ultrasound signals (e.g., ultrasound waves) may be directed to impinge and penetrate a surface of the object at a selected location, where they reflect from the inner structures of the object. By measuring the intensity and position of the reflected ultrasound waves, and analyzing this data with respect to intensity and position of the incident ultrasound waves, details about the relative position and size of these inner structures can be determined.

In medicine, ultrasound may be employed to visualize the size and structure of internal tissues such as muscles and organs, as well as any abnormalities therein (e.g., pathological lesions). For example, ultrasound has been commonly employed for medical imaging due to its relatively low cost, safety, and/or ease of use (e.g., size of equipment, portability, etc.) as compared to other diagnostic imaging techniques such as magnetic resonance imaging (MRI), computed tomographic (CT) imaging, and X-Ray imaging.

Interoperative Ultrasound (IOUS), the use of ultrasound imaging during surgery, has become widely used by surgeons for making decisions in removing tissue during resection operations. Notably, while the surgeon has a defined plan at the start of the operation for the tissue to be removed, circumstances may change during the surgery and/or further clarification may be desirable. Thus, IOUS imaging can be a particularly useful tool in gathering additional information useable by surgeons in making decisions during surgery. New information determined during an intraoperative scan that can improve the likelihood of successful completion of the surgery.

Ultrasound mean attenuation coefficient (MAC) values of tissues are strongly dependent upon the state of health of the tissue. Normal, healthy liver tissue exhibits a MAC value of about 0.53 dB/cm/MHz, on average. In contrast, malignant tumors exhibit lower MAC values than this. For example, hepatocellular carcinomas (HCC), the most common type of liver cancer, exhibit a MAC value of about 0.43 dB/cm/MHz, on average, and metastatic liver tumors exhibit MAC values of about 0.41 dB/cm/MHz, on average. Furthermore, benign tumors may exhibit MAC values both higher than the healthy MAC value and lower than malignant cancers. For example, hepatic adenomas and focal nodular hyperplasia of the liver exhibit MAC values of about 0.66 dB/cm/MHz, on average, and hepatic hemangiomas exhibit an average MAC value of about 0.29 dB/cm/MHz, on average. Thus, MAC value of a tissue (e.g., liver tissue) is an indicator of the condition of the liver.

Attempts to use MAC values for cancer tissue detection have been frustrated to date. For example, while it is possible to display MAC values as an image, where each MAC value is used to shade or color respective regions of interest (ROIs) as projected onto a B-scan or similar image filed, MAC values can vary due to actual variations in tissue characteristics, independent of the presence or absence of cancer. Furthermore, estimation errors may be introduced into measurement of MAC values which are specific to the measurement technique. Thus, owing to complex correlations between the cancerous state of an examined tissue and the MAC values measured for that tissue, use of MAC values (e.g., direct display of MAC values) has not, to date, been used successfully for identification of cancerous tissues.

Provided herein are embodiments that relate to the identification of cancerous tissue by ultrasound. Methods and attendant systems are provided that employ measurements and/or data regarding attenuated ultrasound signals for the identification of cancerous tissues. From measurements of mean attenuation coefficient for respective regions of interest (ROI) of an organism, the disclosed systems and methods can calculate likelihood parameters that are related to the likelihood of a tissue being cancerous. The likelihood parameters can be further used to augment conventional echography displays, such as those used during IOUS imaging, and/or facilitate discernment between cancerous and non-cancerous tissue. In this manner, difficulties previously encountered in the use of MACs for detection of cancerous tissues can be overcome and margins can be more accurately identified during resection.

In embodiments discussed in greater detail below, a detection system can be provided for detection of cancerous tissue. The detection system can obtain ultrasound signals (for example, incident and reflected ultrasound waves) and analyze these ultrasound signals for one or more selected ROIs of an organism. From this analysis, an estimated attenuation coefficient for the ROI can be determined, and the estimated attenuation coefficient can be further employed to calculate the likelihood value ($L_v$). Relatively larger values of the likelihood value ($L_v$) can indicate that it is more likely that the tissue within the ROI is cancerous, while, conversely, relatively lower values of the likelihood value ($L_v$) can indicate that it is less likely that the tissue within the ROI is cancerous. The determined likelihood value ($L_v$) can be displayed as a visual characteristic in an electronic display device (for example, an intensity, a pattern, a color map, a numerical value etc., displayed on an electronic display) to assist in the process of determining whether tissue in the ROI is cancerous or non-cancerous. In some embodiments, the likelihood value ($L_v$) is a likelihood ratio ($L_c$) that can be displayed as the ratio itself over the ROI. In some embodiments, sound or other indicators can be used to denote areas where the tissue is likely to be cancerous.

The detection system can calculate the likelihood value ($L_v$) using MAC values measured for tissue within the ROI using a selected technique and statistical information for the probability distribution of MAC values of the tissue measured using the selected technique (for example, mean, standard deviation). For example, a first probability that the tissue within the ROI is cancerous can be calculated using the measured MAC value in combination with statistical information regarding the MAC when the tissue is cancerous (for example, the mean and standard deviation of a normal MAC probability distribution for the tissue when cancerous). A second probability that the tissue within the ROI is cancerous can be calculated using the measured MAC value in combination with statistical information regarding the MAC when the tissue is not cancerous (for example, the mean and standard deviation of a normal MAC probability distribution for the tissue when not cancerous). From the ratio of the first and second probabilities, the likelihood value ($L_v$), in the form of a likelihood ratio ($L_c$) can be calculated.

To address the complex correlations between the MAC and the cancer state of the tissue, the disclosed detection method can filter the measured MAC results. For example, MAC training data can be obtained for a selected tissue and MAC measuring technique that includes measured MAC values and the state of the tissue (e.g., healthy, cancerous and type of cancer, benign tumor and type of tumor, etc.). From the training data, a critical range of MAC values for cancerous tissue can be identified. In some embodiments, this data can be stored on a computer-readable medium. In some embodiments, this information can be accessed during one or more of the methods provided herein.

This range of MAC values can be used to exclude or filter measured MAC values from further consideration by the detection system. For example, measured MAC values greater than or less than a selected range (for example, outside of 0.39 to 0.56) can be generally associated with non-cancerous tissue (for example, healthy tissue or benign tumors).

In this manner, MAC measurements of tissues predicted to be non-cancerous (or to have a high likelihood of being cancerous) can be removed from consideration prior to further analysis. Thus, even though variations in the MAC can arise due to tissue variations and/or measurement errors, the likelihood that a tissue is falsely identified as being positive for cancer can be reduced. In some embodiments, the likelihood value ($L_v$) can be displayed as a visual characteristic on an ultrasound image, such as an intensity (e.g., a brightness or darkness) or a color map. Such displays can be further presented separately from a standard echocardiogram display or overlaid upon a standard echocardiogram display in order to augment the echocardiogram display. With this augmented display, it can be easier to determine whether tissue being imaged is cancerous or non-cancerous.

In the discussion below, embodiments may be presented in the context of liver tissues. It will be understood by one of ordinary skill in the art, however, that liver tissues are discussed merely for illustration and that the disclosed embodiments may be used to detect cancer in tissue of any type and indeed, can be applied for noncancerous embodiments as well. In some embodiments, the method and/or devices can be employed in any system in which one desires to have information regarding the likelihood ($L_v$ such as a $L_c$) that a region of interest has a MAC that is indicative of, and/or correlated with, a characteristic that is of interest (for example, healthy tissue, cancerous tissue, a non-flesh material, etc.

FIG. 1A illustrates a specific purpose built device 1 for detection of cancer in a region of interest of a tissue. As shown in FIG. 1A, the device can include a data analysis component 122 in communication with a display component 124. The data analysis component 122 can be configured to execute any of the methods, including the equations provided herein, in order to obtain a likelihood value ($L_v$), such as a likelihood ratio ($L_c$). This likelihood value ($L_v$) is then taken by the display component and displayed in some manner. The likelihood value ($L_v$) can be displayed as a numerical value. However, as detailed herein, it can also be displayed as a visual characteristic associated with an ultrasound image, for example, by shading sections of the region of interest having a higher likelihood value ($L_v$) in the color red. In some embodiments, the device 1 can be configured to receive information from an optional ultrasound imaging device 104 and/or an optional data store 110. In some embodiments, one or more of the data analysis component 122, the display component 124, the data store 110, and/or the ultrasound imaging device 104 can be arranged within a single device and/or separated into individual components, such as in a kit or system.

Figure 1B:
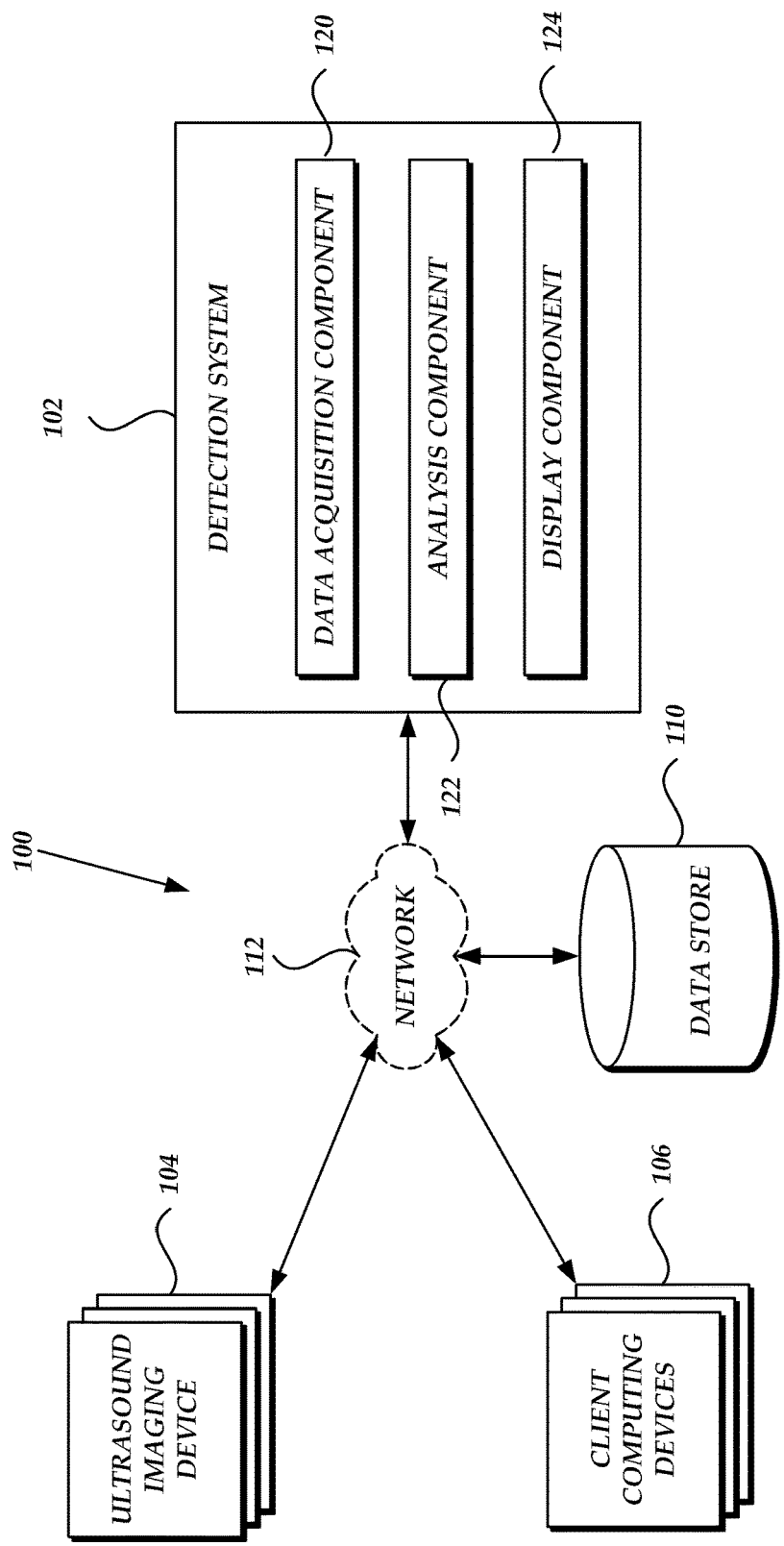
FIG. 1B is a schematic illustration of some embodiments of a cancer detection system.

FIG. 1B is a block diagram depicting some embodiments of an operating environment 100 that allows for detection of cancer in a region of interest of a tissue. For example, the operating environment 100 includes a detection system 102, an ultrasound imaging device 104, a client computing device 106, and a data store 110, each in communication via a network 112. The detection system 102 may obtain ultrasound signals for analysis and identification of cancerous tissue within the ROI. The network 112 need not be included in all embodiments. For example, the ultrasound imaging device 104 can be directly connected the detection system 102. Alternatively, the ultrasound imaging device 104 can be part of and/or integrated with the detection system 102. Alternatively, one or more parts of the detection system 102 can be part of and/or directly connected to the data store 110 and/or the client computing devices 106.

In some embodiments, a user, employing the ultrasound imaging device 104, can acquire ultrasound signals from imaging an ROI of a tissue and transmit the ultrasound signals from the ultrasound imaging device 104 to the detection system 102. In some embodiments, previously acquired ultrasound signals can be transmitted to the detection system from the data store 110. The detection system 102 can analyze the ultrasound signals for respective ROIs in order to identify the cancer likelihood value ($L_v$ or $L_c$) for each ROIs based on measured ultrasound attenuation. Subsequently, the calculated likelihood values can be prepared for display. This display data can be transmitted to the ultrasound imaging device 104 and/or a client computing device 106. As noted above, it need not be transmitted via the network in embodiments in which the parts are otherwise linked to one another.

Alternatively, or in addition, the display data can also be stored in the data store 110. It may be understood that data store 110 can represent one or more data storage devices. The data store 100 can include network-based storage capable of communicating with any component of the environment 100 via the network 112. The data store 100 can further include storage that is in local communication with any component of the environment. The data store 110 need not be included in all embodiments. For example, when one or more parts of the detection system 102 can display the display data, such as the likelihood ratio ($L_c$), the device need not include or be associated with a data store 110.

In some embodiments, the ultrasound imaging device 104 and the client computing devices 106 can communicate with the detection system 102 via the optional network 112. The ultrasound imaging device 104 can include any ultrasound imaging device, as understood by one of ordinary skill in the art.

The client computing devices 106 can include any computing device, such as personal computers (PCs), kiosks, thin clients, home computers, and dedicated or embedded machines. Further examples may include laptop or tablet computers, servers, personal digital assistants (PDAs), hybrid PDA/mobile phones, mobile phones, electronic book readers, set-top boxes, cameras, digital media players, and the like.

Those skilled in the art will appreciate that the network 112 can be any wired network, wireless network, or combinations thereof. In addition, the network 112 can be a personal area network, local area network, wide area network, cable network, satellite network, cellular telephone network, or combinations thereof. In some illustrated embodiments, the network 112 can be the Internet. Protocols and components for communicating via the Internet or any of the other aforementioned types of communication networks are well known to those skilled in the art of computer communications and, thus, are not described in more detail herein.

The detection system 102 is illustrated in FIG. 1B operating in a distributed computing environment comprising several computer systems that are interconnected using one or more networks 112. As noted above, the network 112, is not required in all embodiments, for example, removal of the network 112 allows for direct linking of the imaging device 104 to one or more components in the detection system 102, such as the data acquisition component 120, the analysis component 122, and/or the display component 124. In addition, detection system 102 can include a data acquisition component 120, an analysis component 122, and a display component 124, discussed in greater detail below. However, as will be appreciated by those skilled in the art, the detection system 102 and operating environment 100 may have fewer or greater components than are illustrated in FIG. 1B. Furthermore, in embodiments in which one or more of the parts are directly linked to one another and/or incorporated into a single device, the network 112 need not be present, or employed for transmitting information from one part to another. Thus, the depiction of the detection system 102 in FIG. 1B should be taken as illustrative and not limiting to the present disclosure. For example, in some embodiments, the device and/or system and/or kit need not be in a distributed arrangement. The ultrasound imaging device 104 and the detection system 102 can be integrated into a single device or directly linked devices. The ultrasound imaging device 104 can be part and/or integrated with the data acquisition component 120, the analysis component 122, and/or the display component 124. The single device and/or system can also include the data store 110 and/or the client computing device 106.

Any one or more of the data acquisition component 120, analysis component 122, and display component 124 can be embodied in a plurality of components, each executing an instance of the respective data acquisition component 120, analysis component 122, and display component 124. A server or other computing component implementing any one of data acquisition component 120, analysis component 122, and display component 124 can include a network interface, memory, processing unit, and computer readable medium drive, all of which may communicate which each other may way of a communication bus. The network interface can provide connectivity over the network 112 and/or other networks or computer systems. The processing unit can communicate to and from memory containing program instructions that the processing unit executes in order to operate the respective data acquisition component 120, analysis component 122, and display component 124. The memory can generally include RAM, ROM, and/or other persistent and auxiliary memory.

Figure 2:
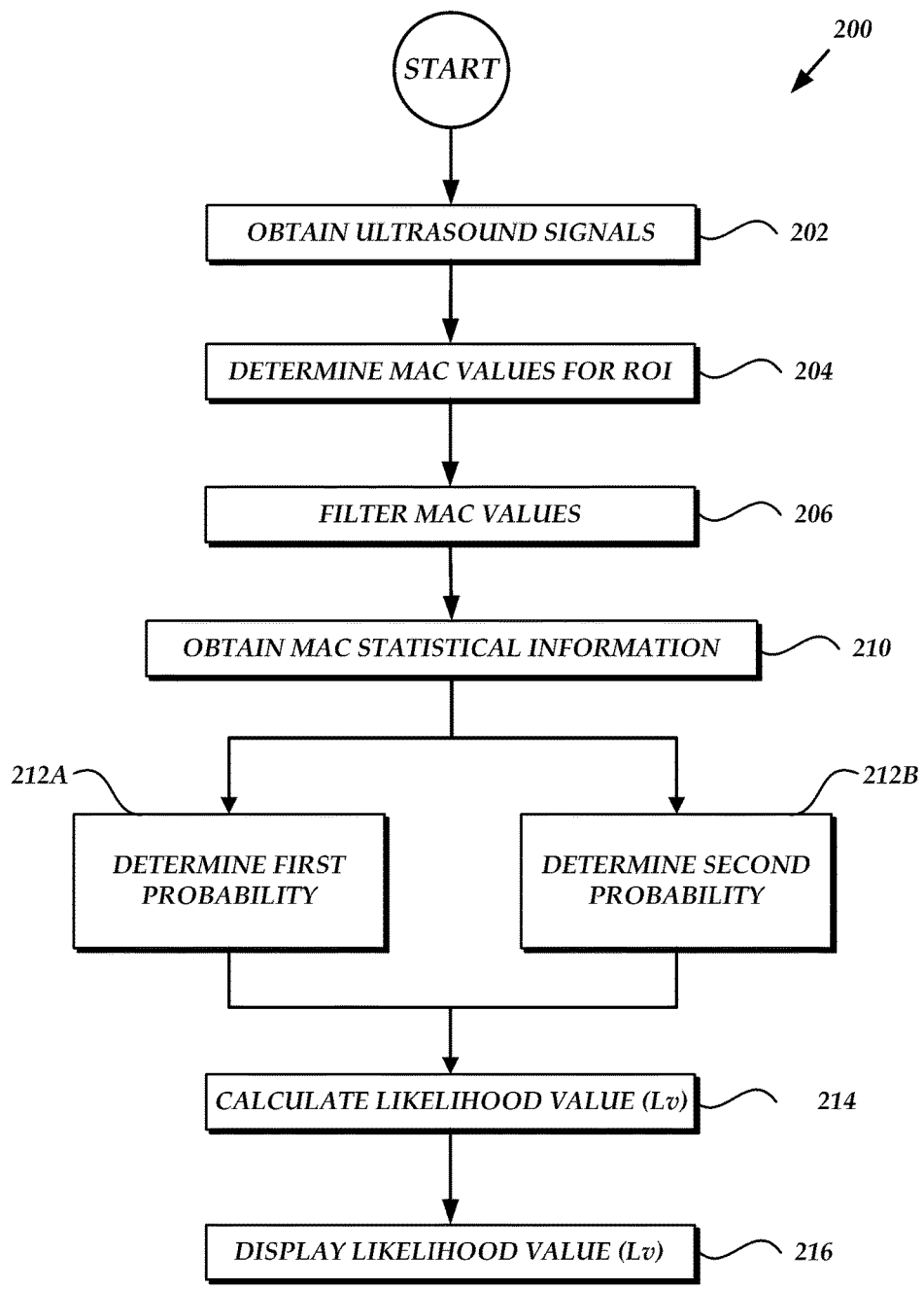
FIG. 2 is a flow diagram illustrating some embodiments of a method of augmenting an echography display and enhancing identification of cancerous tissue.

With further reference to FIGS. 1A, 1B, and 2, illustrative components and respective operations of the detection system 102 will now be discussed. FIG. 2 is a flow diagram illustrating some embodiments of a method 200 of augmenting an echography display and enhancing identification of cancerous tissue. In an operation 202 of the method 200, the data acquisition component 120 can obtain the ultrasound signals from any computing device within the computing environment 100 (e.g., the ultrasound imaging device 104, data store 110, etc.). For example, a user, utilizing the ultrasound imaging device 104, can submit a request to the detection system 102 for analysis and augmentation of measured ultrasound signals in real-time. The request can include the ultrasound signals to be analyzed as well as additional information regarding the ultrasound signals, such as a type of tissue, a reference code for unique identification of the ultrasound signals, etc.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In some embodiments, the ultrasound signals can include ultrasound attenuation information at a selected ROI. For example, the ultrasound signals can include amplitude information for pulsed ultrasound waves that are incident upon the ROI and reflected from the ROI of the tissue under investigation. From this information, attenuation of the ultrasound wave amplitude when traveling through the tissue can be calculated (for example, by the analysis component 120) for each pulse at the ROI. In some embodiments, the ultrasound signals can include the attenuation information for each pulse.

The data acquisition component 120 can transmit this information to the analysis component 122 for analysis. The mean attenuation coefficient (MAC) value of the ultrasound signals at a given ROI can be estimated in operation 204. The present methods and devices are not limited by any particular method of determining a MAC, and, in some embodiments, and method, or combination of methods of determining a MAC can be employed.

There are a number of mathematical methods that can be used for estimating MAC values, particularly for liver tissue. Methods to estimate the acoustic attenuation of soft tissue from pulse echo can be done either in the time-domain or in the frequency-domain, from the exponential decay of the echo envelope or spectra. In general, the time-domain methods are faster and easier to implement for real-time ultrasound measurements than frequency-domain methods. For example, a time-domain method, called the envelope peak (EP) method, has been developed for attenuation in reflection. Use of the EP method can be advantageous owing to higher signal to noise ratio (SNR). Furthermore, faster computation can be achieved with the EP method, as compared with other time domain methods. Additionally, the standard deviation of the EP method can be about 0.21 dB/cm/MHz at about 2 cm, about 0.28 dB/cm/MHz at about 3 cm, and about 0.28 dB/cm/MHz at about 4 cm. As such, use of the EP method can be useful for detection of lesions that are relatively distant. Moreover, techniques used for spectral analysis in the frequency domain, such as autoregressive, autocorrelation, and windowed Fourier transformation can increase the variance of the attenuation estimation. Alternatively, some non-parametric estimation methods exhibit a lower standard deviation at higher frequencies and can be preferred in such cases. Thus, any method of MAC estimation can be employed with the embodiments of the present disclosure, without limit. In some embodiments, the MAC estimation is achieved by one of the above noted methods.

In some embodiments, one or more MAC values can be retrieved from the data store by the analysis component 122.

As discussed above, direct use of MAC values for identifying cancerous regions within the ROI is generally complicated by the fact that the MAC values does not correlate directly to the state of the tissue. To address this issue, some embodiments can include an optional filtering process of the MAC values. For example, in some embodiments, only MAC values that lie within a selected range are used to generate a likelihood value ($L_v$, such as the $L_c$) which is directly related the likelihood of the tissue being cancerous. Notably, in some embodiments, the ROI for tissues exhibiting MAC values outside of the selected range are generally not cancerous and may not be necessary to consider further in various procedures.

In some embodiments, the selected range of MAC values can be retrieved from the data store 110 (e.g., by the data acquisition component 120). In some embodiments, the analysis component 122 can determine the selected range of MAC values from training data. For example, in some embodiments, the selected range of MAC values for cancerous tissue may be about 0.39 dB/cm/MHz to about 0.56 dB/cm/MHz.

In some embodiments, training data can be employed as follows to determine the selected range of MAC values. The training data can be retrieved by one of the data acquisition component 120 and the analysis component 122 (e.g., from data store 110). The training data can include a MAC value for the tissue estimated according to a selected technique and a corresponding state of the tissue (e.g., cancerous, healthy, benign tumor, etc.). From this training data, a range of MAC values can be determined that encompasses at least a portion of the MAC values for cancerous tissues. For example, in some embodiment, the range of MAC values can be selected to encompass all MAC values measured for cancerous tissues in the training data. In another embodiment, the range of MAC values can be the range which captures a selected percentage of MAC values measured for cancerous tissues (e.g., 90%, 95%, 99%, etc.) in the training data. Other criteria for determining the range of MAC values can also be employed with embodiments of the present disclosure, without limit.

In some embodiments, those MAC values that lie outside the selected range can be optionally labeled and directed for further processing. For example, tissues having estimate MAC values higher than the selected range can be labeled as possible hepatic adenoma and focal nodular hyperplasia. Tissues having estimated MAC values lower than the selected range can be labeled as possible hepatic hemangioma. The MAC values for these tissues can be further optionally processed by computer-aided diagnosis pattern recognition methods for finer classification.

The analysis component 222 can determine the first probability that the tissue is cancerous at least based upon the obtained MAC for the ROI and the statistical distribution of MAC for the tissue in a cancerous state. The analysis component can further determine the second probability that the tissue is not cancerous at least based on the obtained MAC for the ROI and statistical information regarding the distribution of the MAC for the tissue in a non-cancerous state. The distribution of the MAC values, and therefore, the statistical information, can have a dependence on one or more of the tissue type and the method by which the MACs are measured. In some embodiments, the statistical information can be based upon a normal distribution of the MAC values. However, it may be understood that any statistical distribution of the MAC values can be used with embodiments of the disclosure, without limit.

In some embodiments, the first and second probabilities can be determined according to Equations (1) and (2):

$$Z_1 = \frac{(X - \mu_1)}{\sigma_1} \quad (1)$$

$$Z_2 = \frac{(X - \mu_2)}{\sigma_2} \quad (2)$$

where X is the MAC value measured for the ROI, $\mu_1$ and $\mu_2$ are the mean of the MAC distribution in cancerous tissue and non-cancerous tissue, respectively, and $\sigma_1$ and $\sigma_2$ are the standard deviation of the MAC distribution in cancerous tissue and non-cancerous tissue, respectively.

The statistical parameters $\mu_1$, $\mu_2$, $\sigma_1$ and $\sigma_2$ can be stored in the data store 110 and retrieved by the analysis component 222 in operation 210 of the method 200. The first and second probabilities $Z_1$ and $Z_2$ can be calculated in operations 212A and 212B.

In some embodiments, limited MAC data may be available (for example, small sample size) and the standard deviation of the MAC may be unknown. A t-test can be used to characterize the uncertainty in variance due to the uncertainty in the MAC estimation calculation itself. The distribution of the t statistic is referred to as the t distribution or the student t distribution. A scale factor, s can be related to the variances of the tissue states by $$s_1^2 = \frac{\sigma_1^2}{n} \text{ and } s_2^2 = \frac{\sigma_2^2}{n},$$

where n is the sample size. The variance of the MAC estimation error $\sigma_{est}^2$ should be added to each of $\sigma_1^2$ and $\sigma_2^2$ in the models of uncertainty in predicting the probability of cancerous tissue or non-cancerous tissue given the estimate value of MAC from the measured signal. Thus, under such circumstances, the first and second probabilities can be given by the student's t score, Equations (3) and (4):

$$T_1 = \frac{(X - \mu_1^*)}{s_1^*} \quad (3)$$

$$T_2 = \frac{(X - \mu_2^*)}{s_2^*} \quad (4)$$

where $\mu^*_1$ and $\mu^*_2$ are the experimental observed mean values of the MAC plus the estimation bias for the method selected to obtain the MAC and $s^*_1$ and $s^*_2$ are each given by the square root of the sum of the standard deviation of the measurement squared and the estimation error variance.

The probability of the tissue being cancerous and non-cancerous, given the measured MAC value X, can be found using the distribution for the probabilities of $Z_1$ and $Z_2$ (normal distribution) or $T_1$ and $T_2$ (student distribution). The likelihood ratio ($L_c$) can be calculated in operation 214 from the ratio of the first and second probabilities, Equation (5):

$$L_c = \frac{Z_1(X, \mu_1, \sigma_1)}{Z_2(X, \mu_2, \sigma_2)} \text{ or } \frac{T_1(X, \mu_1^*, \sigma_1^*)}{T_2(X, \mu_2^*, \sigma_2^*)} \quad (5)$$

While equation (5) outlines one embodiment for determining a likelihood ratio ($L_c$), other methods, equations, and/or further manipulations of the $L_c$ can also be employed in order to determine the likelihood ratio for a particular region of interest. In particular, different formulae can be used to determine the likelihood ratio ($L_c$). In some embodiments, any equation or method for determining a likelihood can be used and thus likelihood values ($L_V$) in general can be employed. In some embodiments, the likelihood value ($L_V$) can be transmitted to the display component by the analysis component. In operation 216, the display component can generate a display for presentation of the likelihood value ($L_V$) to a user. In certain embodiments, the likelihood value ($L_V$) can be used to shade or color the region of interest that corresponds to the measured value of the MAC. In some embodiments, the likelihood value ($L_V$) can be displayed as an overlay to an echogram or displayed separately.

Figure 3:
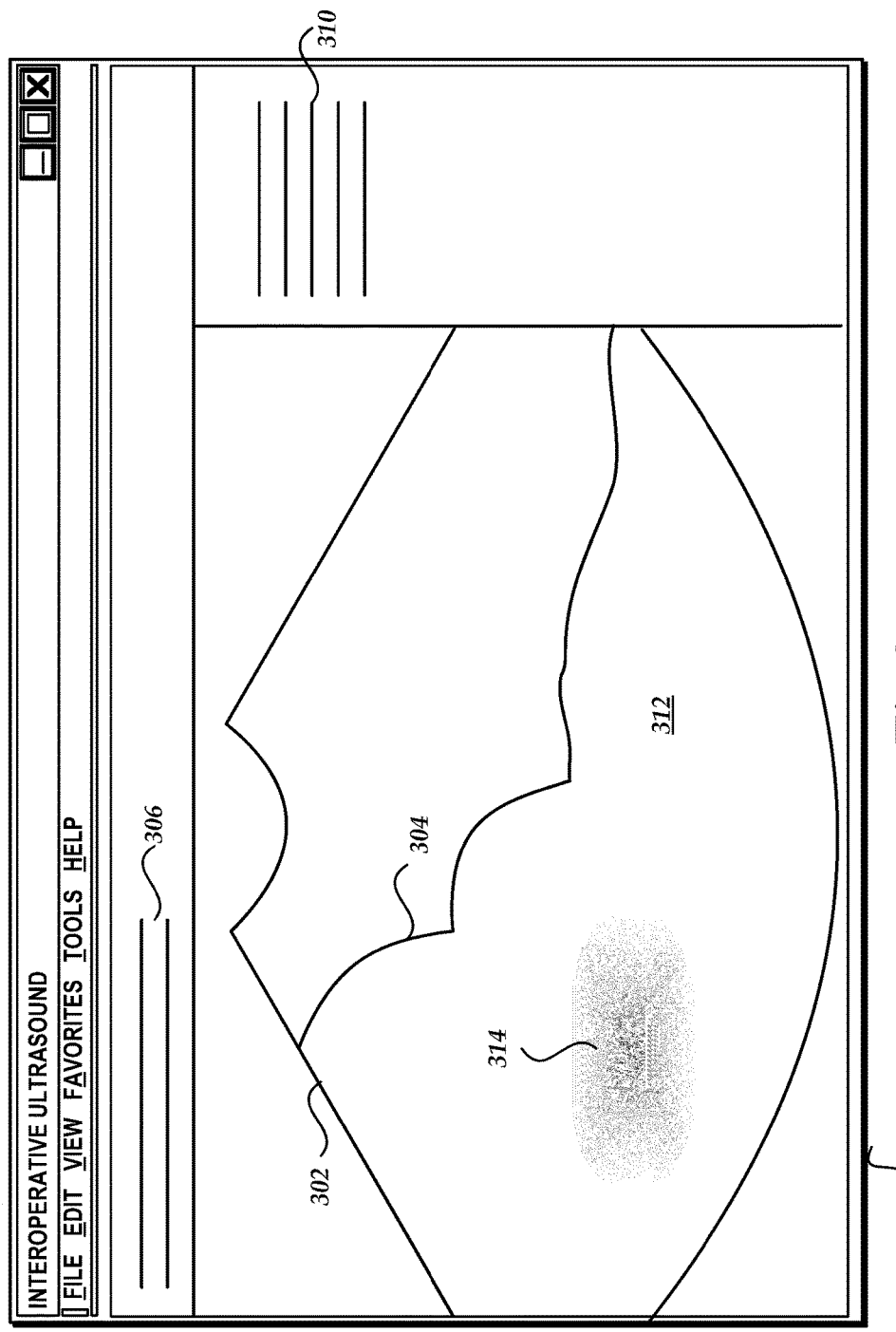
FIG. 3 is a schematic illustration of some embodiments of an echography display including an augmented display.

An example display 300 including a representation of the likelihood value ($L_V$) is illustrated in FIG. 3. The display 300 includes an echograph 302 of a tissue 304 and information fields 310 and 306. Information field 306 can display bibliographic information regarding the echograph, including, but not limited to, a patient's name, an operator or user's name, a date of the echograph, a time of the echograph, and the like. The information field 310 can display operating information regarding the echograph, including, but not limited to, an operating frequency, signal strength, relative position, and the like.

The echograph 302 can further be augmented or annotated with the likelihood value ($L_V$). For example, in some embodiments, the likelihood value ($L_V$) is configured to be displayed as shading, from light to dark, where the relatively light areas represent low likelihood values ($L_V$) that are unlikely to be cancerous and the relatively dark areas represent high likelihood values ($L_V$) that are likely to be cancerous. As illustrated in FIG. 3, region 312 of the tissue 304 is relatively light and, therefore, unlikely to be cancerous. In contrast, region 314 of the tissue 304 is relatively dark at its center and likely to be cancerous. Moving outward from the center, the tissue in region 314 becomes lighter and is less likely to be cancerous than the tissue in the center. With a real-time display such as display 300, a surgeon can determine that region 314 of the tissue 304 has a higher likelihood of being cancerous than the surrounding region 312 of the tissue 304.

The term ultrasound, as discussed herein, can include its ordinary meaning as understood in the art of acoustics and can further include any cyclic, sound pressure with a frequency higher than the upper limit of human hearing. Examples of ultrasound can include, but are not limited to, ultrasound employed in medical sonography (ultrasonography).

Embodiments of the present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. Examples of computer-readable media may include, but are not limited to, optical storage devices, magnetic storage devices, electrical (e.g., solid state) storage devices, and the like and combinations thereof. Such computer-readable media may be volatile storage devices, non-volatile storage devices, and combinations thereof. The computer-readable instructions can be executed by a processor of an electronic device, including, but not limited to, mobile computing devices, network computing elements, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description may set forth various embodiments of the disclosed devices and/or processes using block diagrams, flowcharts, and/or examples. Insofar as such block diagrams, flowcharts, and/or examples contain one or more functions and/or operations, it may be understood by one of ordinary skill in the art that one or more functions and/or operations within such block diagrams, flowcharts, and/or examples can be implemented, individually and/or collectively, by a wide range of hardware, software, firmware, or virtually any combination thereof.

In one embodiment, at least a portion of the subject matter described herein may be implemented by one or more of Application Specific Integrated Circuits (ASICs), Field Programmable Gate Arrays (FPGAs), digital signal processors (DSPs), and other integrated formats. However, one of ordinary skill in the art may recognize that selected aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

In addition, one of ordinary skill in the art may appreciate that embodiments of the mechanisms described herein may be capable of being distributed as a program product in a variety of forms. An embodiment of the subject matter described herein may be employed regardless of the particular type of signal bearing medium used to actually carry out the distribution. Examples of a signal bearing medium include, but are not limited to, a recordable media such as floppy disks, hard disk drives, compact discs (CD), digital versatile/video disc DVD, digital tapes, computer memories, etc. A transmission-type medium such as a digital and/or an analog communication medium (e.g., fiber optic cables, waveguides, wired communications links, wireless communication links, etc.).

One of ordinary skill in the art may also recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation.

One of ordinary skill in the art may recognize that a data processing system may include one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A data processing system may be implemented utilizing any suitable commercially available components, such as those typically found in data computing/communication and/or network computing/communication systems.

Embodiments of the disclosure may illustrate different components contained within, or connected with, different other components. It may be understood that such depicted architectures are merely examples, and that many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components.

Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

The computer may operate in a networked environment using logical connections to one or more computers, such as a remote computer connected to network interface. The remote computer may be a personal computer, a server, a router, a network PC, a peer device or other common network node, and can include many or all of the elements described above relative to computer. Networking environments are commonplace in offices, enterprise-wide area networks (WAN), local area networks (LAN), intranets and the Internet. For example, in the subject matter of the present application, computer may comprise the source machine from which data is being migrated, and the remote computer may comprise the destination machine or vice versa. Note however, that source and destination machines need not be connected by a network or any other means, but instead, data may be migrated via any media capable of being written by the source platform and read by the destination platform or platforms. When used in a LAN or WLAN networking environment, computer is connected to the LAN through a network interface or an adapter. When used in a WAN networking environment, computer typically includes a modem or other means for establishing communications over the WAN, such as the Internet or network. It will be appreciated that other means of establishing a communications link between the computers may be used.

According to some embodiments, the computer is connected in a networking environment such that the processor and/or program modules can perform with or as augmentation for ultrasound visualization in accordance with embodiments herein.

FIG. 4 is a block diagram illustrating an example computing device 500 that is arranged for augmentation of ultrasound visualization in accordance with the present disclosure. In a very basic configuration 502, computing device 500 typically includes one or more processors 504 and a system memory 506. A memory bus 508 may be used for communicating between processor 504 and system memory 506.

Depending on the desired configuration, processor 504 may be of any type including but not limited to a microprocessor (μP), a microcontroller (μC), a digital signal processor (DSP), or any combination thereof. Processor 504 may include one more levels of caching, such as a level one cache 510 and a level two cache 512, a processor core 514, and registers 516. An example processor core 514 may include an arithmetic logic unit (ALU), a floating point unit (FPU), a digital signal processing core (DSP Core), or any combination thereof. An example memory controller 518 may also be used with processor 504, or in some implementations memory controller 518 may be an internal part of processor 504.

Depending on the desired configuration, system memory 506 may be of any type including but not limited to volatile memory (such as RAM), non-volatile memory (such as ROM, flash memory, etc.) or any combination thereof. System memory 506 may include an operating system 520, one or more applications 522, and program data 524. Application 522 may include an augmentation method or algorithm therefore 526 that is arranged to perform the functions as described herein, including those described with respect to process 200 of FIG. 2 and/or the processes outlined in FIG. 6 (for example, 720, 730, 745, 740, 750, and/or 760). Program data 524 may include augmentation data 528 (for example, involving the likelihood value ($L_V$) and/or likelihood ratio ($L_c$)) that may be useful for operation with the augmentation method as is described herein. In some embodiments, application 522 may be arranged to operate with program data 524 on operating system 520 such that an augmented ultrasound image can be provided, such as, for example, by displaying the likelihood value ($L_V$) for the corresponding area (or an appropriate visual characteristic for the likelihood value), as described herein. This described basic configuration 502 is illustrated in FIG. 4 by those components within the inner dashed line. As described herein, rather than merely a numerical likelihood value ($L_v$), the likelihood value can be displayed as a visual characteristic to an end user. This conversion can occur at any number of locations, for example, within Application 522, the processor 504, or elsewhere. The visual characteristic can be displayed and/or combined with the output ultrasound image (for example, by assigning an appropriate visual characteristic (such as the color red) to an area of an image with a high likelihood value ($L_v$)). In some embodiments, the ultrasound equipment, such as the ultrasound transducer 700, RF transmitter 706, and RF receiver 705 (including optional T/R switch 701), return pulse detector 710 (see FIG. 6), can be in communication with the computing device 500 (see FIG. 4), for example via the peripheral interfaces 544 and/or as the other computing devices 562. In some embodiments, they are combined as a single device.

Computing device 500 may have additional features or functionality, and additional interfaces to facilitate communications between basic configuration 502 and any required devices and interfaces. For example, a bus/interface controller 530 may be used to facilitate communications between basic configuration 502 and one or more data storage devices 532 via a storage interface bus 534. Data storage devices 532 may be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 506, removable storage devices 536 and non-removable storage devices 538 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of computing device 500.

Computing device 500 may also include an interface bus 540 for facilitating communication from various interface devices (e.g., output devices 542, peripheral interfaces 544, and communication devices 546) to basic configuration 502 via bus/interface controller 530. Example output devices 542 include a graphics processing unit 548 and an audio processing unit 550, which may be configured to communicate to various external devices such as a display or speakers via one or more A/V ports 552. Example peripheral interfaces 544 include a serial interface controller 554 or a parallel interface controller 556, which may be configured to communicate with external devices such as input devices (e.g., keyboard, mouse, pen, voice input device, touch input device, an ultrasound device, etc.) or other peripheral devices (e.g., printer, scanner, etc.) via one or more I/O ports 958. An example communication device 546 includes a network controller 560, which may be arranged to facilitate communications with one or more other computing devices 562 over a network communication link via one or more communication ports 564.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations.

FIG. 5 illustrates an example computer program product 600 arranged in accordance with at least some examples of the present disclosure. Program product 600 may include a signal bearing medium 602. Signal bearing medium 602 may include one or more instructions 604 that, when executed by, for example, a processor, may provide the functionality described above with respect to FIGS. 1A, 1B, 2, and 6. Thus, for example, referring to system 100, one or more of modules 104, 106, 102, 120, 122, 124, and/or 110 may undertake one or more of the blocks shown in FIGS. 1A, 1B, 2, and 6 in response to instructions 604 conveyed to the system 100 by medium 602.

In some implementations, signal bearing medium 602 may encompass a computer-readable medium 606, such as, but not limited to, a hard disk drive, a Compact Disc (CD), a Digital Video Disk (DVD), a digital tape, memory, etc. In some implementations, signal bearing medium 602 may encompass a recordable medium 608, such as, but not limited to, memory, read/write (R/W) CDs, R/W DVDs, etc. In some implementations, signal bearing medium 602 may encompass a communications medium 610, such as, but not limited to, a digital and/or an analog communication medium (e.g., a fiber optic cable, a waveguide, a wired communications link, a wireless communication link, etc.). Thus, for example, program product 600 may be conveyed to one or more modules of the system 100 by an RF signal bearing medium 602, where the signal bearing medium 602 is conveyed by a wireless communications medium 610 (e.g., a wireless communications medium conforming with the IEEE 802.11 standard).

Figure 6:
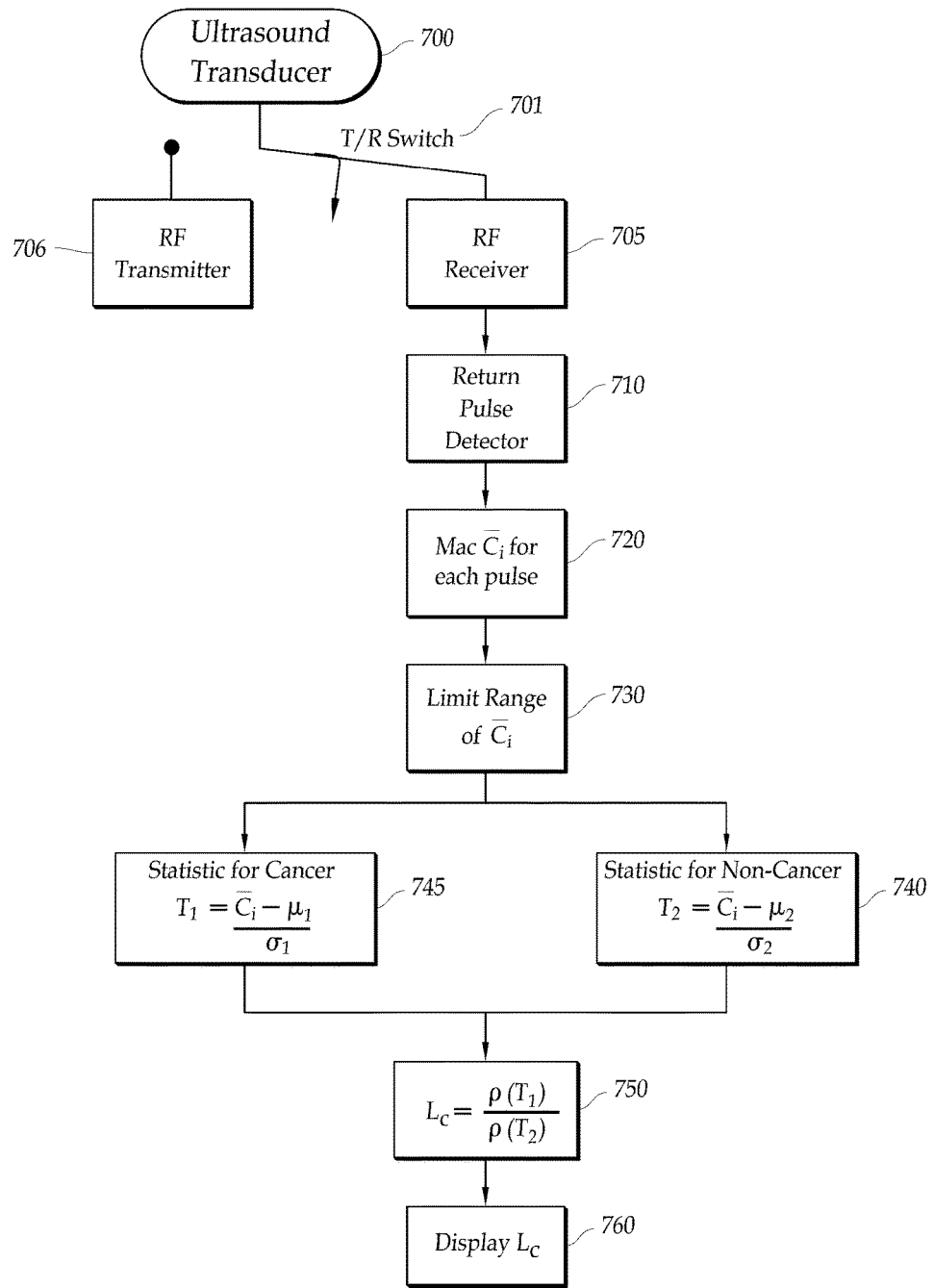
FIG. 6 is a schematic illustration of some embodiments of a system and/or method for generating a likelihood ratio ($L_c$).

FIG. 6 depicts an arrangement of some embodiments of the systems and/or methods provided herein. As shown in FIG. 6, the system and/or method can include an ultrasound transducer 700, which can be in communication with an RF transmitter 706 and/or a RF receiver 705. There can be an optional transmit/receive ("T/R") switch 701 positioned in the system as well. This can be configured to control the flow of information to and/or from the transducer 700. The RF receiver 705 can be linked to a return pulse detector 710, from which a MAC, $C_i$ can be generated for each pulse (block 720). The limit range of $C_i$ can be determined (block 730). Based on this data, a probability that the sample is cancerous can be generated (block 745), as well as a probability that the sample is non-cancerous tissue (block 740). From this, a likelihood ratio ($L_c$) can be generated (block 750), and the likelihood ratio ($L_c$) provided, for example by providing an indicator of the likelihood ratio ($L_c$) on a display (block 760). The indicator of the likelihood ratio ($L_c$) can be presented as a numerical value, shading, coloring, contrast, etc, over and/or associated with the other ultrasound imaging data and/or image.

EXAMPLES

Example 1

Method of Identifying a Cancerous Tissue

An augmented echography display is provided during intraoperative ultrasound (IOUS) imaging to enhance a user's ability to discern between cancerous and non-cancerous tissue in the liver.

An ultrasound signal is taken for a particular section of liver tissue, in vivo, and the signal is processed to extract an estimate of the mean attenuation coefficient for the region from which the signal is taken by using the envelop peak (EP) method. The processed information is then used to provide a likelihood ratio ($L_c$) by dividing the probability of measuring the attenuation coefficient from cancerous tissue by the probability of obtaining the same measurement from a non-cancerous tissue. The likelihood ratio ($L_c$) for the liver tissue is determined to be 90%.

The likelihood ratio ($L_c$) is displayed on the IOUS display by darkening the section of liver tissue from which the data was collected, indicating a higher likelihood that the noted section is cancerous, thereby enhancing the user's ability to discern between cancerous and non-cancerous tissue.

Example 2

Method of Identifying a Cancerous Tissue

An ultrasound signal is taken for a particular section of liver tissue, in vivo, and the signal is processed to extract an estimate of the mean attenuation coefficient (MAC) for the region from which the signal is taken by using the envelop peak (EP) method. One-hundred MAC values are determined. Of the one hundred values, 80 of them fall between 0.39 and 0.56 and the remaining 20 fall outside of that range. The data points falling outside of the 0.39 to 0.56 range are removed, and the rest of the data points are used to provide a likelihood ratio ($L_c$) by dividing the probability of measuring the attenuation coefficient from cancerous tissue by the probability of obtaining the same measurement from a non-cancerous tissue. The likelihood ratio ($L_c$) for the liver tissue is determined to be 99%.

The likelihood ratio ($L_c$) is displayed on the IOUS display by coloring the section of liver tissue from which the data was collected in red, indicating a higher likelihood that the noted section is cancerous, thereby enhancing the user's ability to discern between cancerous and non-cancerous tissue.

Example 3

Method of Preparing a Training Set

Ten livers, each having identified tumors, have their identified tumors scanned by ultrasound to obtain 10 mean attenuation coefficient values for the tumors (as the ROI), using the envelop peak method. These values are used to establish a range of MAC values that are indicative of a cancerous tissue.

Ten livers, each being free of tumors, are scanned by ultrasound to obtain 10 mean attenuation coefficient values, using the envelop peak method. These values are used to establish a range of MAC values that are indicative of a non-cancerous tissue.

The values can then be used, as appropriate, for determining a likelihood that values derived from the envelop peak method in a different tumor is cancerous.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It may be understood by one of ordinary skill the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It may be further understood by one of ordinary skill in the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, one of ordinary skill in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It may be further understood by one of ordinary skill the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, one of ordinary skill in the art may recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like may include the number recited and may further refer to ranges which can be subsequently broken down into sub-ranges as discussed above. Finally, as will be understood by one skilled in the art, a range may include each individual member. Thus, for example, a group having 1-3 cells may refer to groups having 1, 2, or 3 cells. Similarly, a group having 1-5 cells may refer to groups having 1, 2, 3, 4, or 5 cells, and so forth.

Embodiments of the present disclosure may not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

What is claimed is:

1. An imaging system that improves identification of cancerous tissue, comprising:
   a data store that maintains statistical information regarding a distribution of mean attenuation coefficients of ultrasound signals for a plurality of tissues, wherein the plurality of tissues are in a cancerous state or a non-cancerous state;
   a computing device in communication with the data store, the computing device operative to:
      obtain a mean attenuation coefficient representing attenuation of an ultrasound signal incident upon a region of interest of a tissue;
      determine a first probability that the tissue is cancerous, wherein the first probability is determined based at least upon the obtained mean attenuation coefficient and corresponding statistical mean attenuation coefficient information for the tissue in the cancerous state maintained in the data store;
      determine a second probability that the tissue is non-cancerous, wherein the second probability is determined at least based upon the obtained mean attenuation coefficient and the corresponding statistical mean attenuation coefficient information for the tissue in the non-cancerous state maintained in the data store;
      generate a likelihood value ($L_v$) that the tissue is cancerous based upon the first and second probabilities, wherein the $L_v$ includes a likelihood ratio ($L_c$), and wherein the $L_c$ is a ratio of the first and second probabilities; and
      update the $L_v$ in response to receiving an updated ultrasound signal during resection of the tissue; and
   a display component in communication with the computing device, wherein the display component is configured to:
      display the $L_v$ in real-time as an overlay to an echogram, wherein the $L_v$ facilitates discernment between cancerous and non-cancerous tissue;
      mark via intensity or color map, in the echogram having the $L_v$ displayed thereon as the overlay, the non-cancerous tissue and the cancerous tissue, if any; and
      update the overlay in real time based on the updated $L_v$ to include an updated intensity or an updated color map, wherein updating the overlay to include the updated intensity or the updated color map results in a real-time identification of margins during resection.

2. The system of claim 1, wherein the computing device is further operative to output display data for display of the $L_v$ as a visual characteristic.

3. The system of claim 2, wherein the computing device outputs the visual characteristic concurrently with a display of Intraoperative Ultrasound Imaging (IOUS) data.

4. The system of claim 1, wherein the computing device is in communication with an ultrasound device.

5. The system of claim 4, wherein the computing device is further operative to:
   receive the ultrasound signal from the ultrasound device; and
   analyze the ultrasound signal to obtain the mean attenuation coefficient.

6. A computer-implemented method that improves identification of cancerous tissue, the method comprising:
   maintaining a data store of statistical information regarding a distribution of mean attention coefficients of ultrasound signals for a plurality of tissues, wherein the plurality of tissues are in a cancerous state or a non-cancerous state;
   obtaining, by a computing device, a mean attenuation coefficient representing attenuation of an ultrasound signal incident upon a region of interest of a tissue;
   determining a first probability that the tissue is cancerous, wherein the first probability is determined based at least upon the obtained mean attenuation coefficient and corresponding statistical mean attenuation coefficient information for the tissue in the cancerous state maintained in the data store;
   determining a second probability that the tissue is non-cancerous, wherein the second probability is determined at least based upon the obtained mean attenuation coefficient and the corresponding statistical mean attenuation coefficient information for the tissue in the non-cancerous state maintained in the data store;
   determining, by the computing device, a likelihood value ($L_v$) that the tissue is cancerous based upon the first and second probabilities, wherein the $L_v$ includes a likelihood ratio ($L_c$), and wherein the $L_c$ is a ratio of the first and second probabilities;
   updating the $L_v$ in response to receiving an updated ultrasound signal during resection of the tissue;
   displaying the $L_v$ in real-time as an overlay to an echogram, wherein the $L_v$ facilitates discernment between cancerous and non-cancerous tissue;
   marking via intensity or color map, in the echogram having the $L_v$ displayed thereon as the overlay, the non-cancerous tissue and the cancerous tissue, if any; and
   updating the overlay in real time based on the updated $L_v$ to include an updated intensity or an updated color map, wherein updating the overlay to include the updated intensity or the updated color map results in a real-time identification of margins during resection.

7. The computer-implemented method of claim 6, wherein determining the first probability employs a mean and a standard deviation of a distribution of mean attenuation coefficients in the tissue when in the cancerous state.

8. The computer-implemented method of claim 6, wherein determining the second probability employs a mean and a standard deviation of a distribution of mean attenuation coefficients in the tissue in the non-cancerous state.

9. The computer-implemented method of claim 6, further comprising output of display data configured for display of the $L_v$ as a visual characteristic.

10. The computer-implemented method of claim 6, further comprising obtaining an estimate of the mean attenuation coefficient from analysis of a received ultrasound signal.

11. The computer-implemented method of claim 10, wherein the received ultrasound signal is analyzed in one of a time-domain and a frequency-domain.

12. The computer-implemented method of claim 6, further comprising:
determining that the mean attenuation coefficient is outside of a selected range; and
not determining the $L_v$ from the mean attenuation coefficient.

13. The computer-implemented method of claim 12, wherein the selected range is between 0.39 and 0.56.

14. The computer-implemented method of claim 12, wherein the $L_v$ is the $L_c$, which is defined by equation (5):

$$L_c = \frac{Z_1(X, \mu_1, \sigma_1)}{Z_2(X, \mu_2, \sigma_2)} \text{ or } \frac{T_1(X, \mu_1^*, \sigma_1^*)}{T_2(X, \mu_2^*, \sigma_2^*)}. \quad \text{Equation (5)}$$

wherein $Z_1$ represents the first probability, $Z_2$ represents the second probability, X represents the measured mean attention coefficient (MAC) value, $\mu_1$ represents a first mean of the MAC value, $\mu_2$ represents a second mean of the MAC value, $\sigma_1$ represents a standard deviation of the MAC distribution in cancerous tissue, $\sigma_2$ represents a standard deviation of the MAC distribution in non-cancerous tissue, $T_1$ represents a first student's t score, and $T_2$ represents a second student's t score.

15. A non-transitory computer-readable medium storing software instructions that are readable by a computing system, wherein the software instructions are executable on the computing system in order to cause the computing system to perform operations comprising:
maintaining a data store of statistical information regarding a distribution of mean attention coefficients of ultrasound signals for a plurality of tissues, wherein the plurality of tissues are in a cancerous state or a non-cancerous state;
obtaining a mean attenuation coefficient representing attenuation of an ultrasound signal incident upon a region of interest of a tissue;
determining a first probability that the tissue is cancerous, wherein the first probability is determined based at least upon the obtained mean attenuation coefficient and corresponding statistical mean attenuation coefficient information for the tissue in the cancerous state maintained in the data store;
determining a second probability that the tissue is non-cancerous, wherein the second probability is determined at least based upon the obtained mean attenuation coefficient and the corresponding statistical mean attenuation coefficient information for the tissue in the non-cancerous state maintained in the data store;
generating a likelihood value ($L_v$) that the tissue is cancerous based upon the first and second probabilities, wherein the $L_v$ includes a likelihood ratio ($L_c$), and wherein the $L_c$ is a ratio of the first and second probabilities;
updating the $L_v$ in response to receiving an updated ultrasound signal during resection of the tissue;
displaying the $L_v$ in real-time as an overlay to an echogram, wherein the $L_v$ facilitates discernment between cancerous and non-cancerous tissue;
marking via intensity or color map, in the echogram having the $L_v$ displayed thereon as the overlay, the non-cancerous tissue and the cancerous tissue, if any; and
updating the overlay in real time based on the updated $L_v$ to include an updated intensity or an updated color map, wherein updating the overlay to include the updated intensity or the updated color map results in a real-time identification of margins during resection.

16. The non-transitory computer-readable medium of claim 15, wherein the computing system is in communication with an ultrasound device.

17. The non-transitory computer-readable medium of claim 15, wherein the $L_v$ is the $L_c$.

18. The non-transitory computer-readable medium of claim 17, wherein the $L_c$ is defined by equation (5):

$$L_c = \frac{Z_1(X, \mu_1, \sigma_1)}{Z_2(X, \mu_2, \sigma_2)} \text{ or } \frac{T_1(X, \mu_1^*, \sigma_1^*)}{T_2(X, \mu_2^*, \sigma_2^*)} \quad \text{Equation (5)}$$

wherein $Z_1$ represents the first probability, $Z_2$ represents the second probability, X represents the measured mean attention coefficient (MAC) value, $\mu_1$ represents a first mean of the MAC value, $\mu_2$ represents a second mean of the MAC value, $\sigma_1$ represents a standard deviation of the MAC distribution in cancerous tissue, $\sigma_2$ represents a standard deviation of the MAC distribution in non-cancerous tissue, $T_1$ represents a first student's t score, and $T_2$ represents a second student's t score.

19. The non-transitory computer-readable medium of claim 15, wherein the computing system is further operative to output display data for display of the $L_v$ as a visual characteristic.

20. The non-transitory computer-readable medium of claim 19, wherein the visual characteristic comprises at least one of an intensity and a color.

21. The non-transitory computer-readable medium of claim 20, wherein the operations further comprise displaying the $L_v$ for display concurrently with Intraoperative Ultrasound Imaging (IOUS) data.

22. The non-transitory computer-readable medium of claim 21, wherein the $L_v$ is overlaid with the IOUS data in a display.

* * * * *